United States Patent [19]

Lang

[11] Patent Number: 4,826,832

[45] Date of Patent: May 2, 1989

[54] PENEN COMPOUNDS

[75] Inventor: Marc Lang, Rixheim, France

[73] Assignee: Ciba-Geigy Corporation, Ardsley, N.Y.

[21] Appl. No.: 42,768

[22] Filed: Apr. 27, 1987

[30] Foreign Application Priority Data

May 6, 1986 [CH] Switzerland ............... 1846/86

[51] Int. Cl.⁴ ............... C07D 499/00; A61K 31/425
[52] U.S. Cl. ............... 514/192; 514/195; 540/310
[58] Field of Search ............... 540/310; 514/192, 195, 514/210

[56] References Cited

U.S. PATENT DOCUMENTS

| | | | |
|---|---|---|---|
| 4,272,437 | 6/1981 | Ménard et al. | 260/239 A |
| 4,386,030 | 5/1983 | Christensen et al. | 260/245.2 R |
| 4,540,580 | 9/1985 | Aponso et al. | 514/195 |
| 4,617,300 | 10/1986 | Girijavallabhan et al. | 514/192 |
| 4,623,643 | 11/1986 | Alpegiani et al. | 540/310 |

FOREIGN PATENT DOCUMENTS

| | | |
|---|---|---|
| 0003960 | 9/1979 | European Pat. Off. |
| 0070204 | 1/1983 | European Pat. Off. |
| 0072014 | 2/1983 | European Pat. Off. |
| 0109044 | 5/1984 | European Pat. Off. |
| 0109362 | 6/1984 | European Pat. Off. |
| 148128 | 7/1985 | European Pat. Off. |
| 199675 | 10/1986 | European Pat. Off. |

Primary Examiner—Nicholas S. Rizzo
Attorney, Agent, or Firm—Irving M. Fishman; JoAnn Villamizar

[57] ABSTRACT

Compounds of the formula

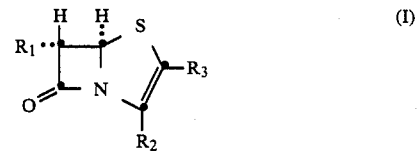

in which $R_1$ represents lower alkyl substituted by hydroxy or by protected hydroxy, $R_2$ represents carboxy or functionally modified carboxy, and $R_3$ represents optionally substituted 3-pyridyl or optionally substituted 4-pyridyl, and pharmaceutically acceptable salts of such compounds, have antibacterial activity. The compounds of the formula I can be manufactured according to processes known per se.

11 Claims, No Drawings

PENEN COMPOUNDS

The invention relates to 2-pyridyl-penem compounds of the formula

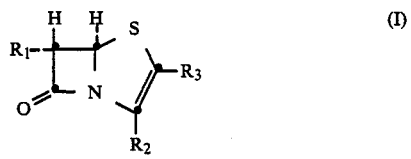

in which $R_1$ represents lower alkyl substituted by hydroxy or by protected hydroxy, $R_2$ represents carboxy or functionally modified carboxy, and $R_3$ represents optionally substituted 3-pyridyl or optionally substituted 4-pyridyl, to salts of compounds of the formula I that have a salt-forming group, to processes for the manufacture of compounds of the formula I, to pharmaceutical preparations that contain such compounds, and to their use for the manufacture of pharmaceutical preparations or as active ingredients in medicaments.

Within the scope of this description, the definitions used hereinbefore and hereinafter preferably have the following meanings:

Functionally modified carboxy $R_2$ is especially esterified carboxy cleavable under physiological conditions, or protected carboxy $R_2'$.

Esterified carboxy groups $R_2$ cleavable (that is to say metabolisable) under physiological conditions are known from cephalosporin, penicillin and penem chemistry. Suitable groups are especially acyloxymethoxycarbonyl groups in which acyl is, for example, the radical of an organic carboxylic acid, especially an optionally substituted lower alkanecarboxylic acid, or in which acyloxymethyl forms the radical of a lactone. Such groups are, for example, lower alkanoyloxymethoxycarbonyl, amino-lower alkanoyloxymethoxycarbonyl, especially α-amino-lower alkanoyloxymethoxycarbonyl, and 4-crotonolactonyl. Other esterified carboxy groups $R_2$ cleavable under physiological conditions are, for example, 5-indanyloxycarbonyl, phthalidyloxycarbonyl, 1-lower alkoxycarbonyloxy-lower alkoxycarbonyl, 1-lower alkoxy-lower alkoxycarbonyl, or also 2-oxo-1,3-dioxolen-4-ylmethoxycarbonyl which is optionally substituted in the 5-position of the dioxolene ring by lower alkyl or phenyl.

3- or 4-pyridyl radicals $R_3$ are unsubstituted or may be substituted, such as, especially, mono- or alternatively poly-substituted, more especially mono- or di-substituted, for example by optionally etherified or esterified hydroxy, for example hydroxy, lower alkoxy, amino-lower alkoxy, lower alkanoyloxy or halogen, by optionally etherified mercapto, for example mercapto, lower alkylthio, amino-lower alkylthio or phenylthio, by lower alkyl, by substituted lower alkyl, such as hydroxy-lower alkyl, lower alkanoyloxy-lower alkyl, carboxy-lower alkyl, lower alkoxycarbonyl-lower alkyl, cyano- or amino-substituted lower alkoxycarbonyl-lower alkyl, carbamoyl-lower alkyl, carbamoyloxy-lower alkyl, cyano-lower alkyl, halo-lower alkyl, optionally N-lower alkylated amino-lower alkyl, for example amino-lower alkyl, lower alkylamino-lower alkyl or di-lower alkylamino-lower alkyl, lower alkanoylamino-lower alkyl, amino-carboxy-lower alkyl and sulpho-lower alkyl, by optionally substituted amino, for example amino, lower alkylamino, di-lower alkylamino or acylamino, such as lower alkanoylamino, by optionally functionally modified carboxy or sulpho, for example carboxy, esterified carboxy, such as lower alkoxycarbonyl or cyano- or amino-substituted lower alkoxycarbonyl, optionally N-lower alkylated carbamoyl, such as carbamoyl, cyano, sulpho or sulphamoyl, by oxido and/or by optionally lower alkyl-, lower alkoxy- and/or halo-substituted phenyl.

The substituents are bonded especially to carbon atoms of the pyridyl radical $R_3$, but may also, such as, especially, in the case of lower alkyl optionally substituted as indicated, or oxido, be bonded to the pyridyl nitrogen atom.

In this description, the term "lower" used in connection with definitions of groups and compounds denotes, unless expressly defined otherwise, that the groups and compounds so designated contain from 1 to 7, preferably from 1 to 4, carbon atoms.

Hydroxy-substituted lower alkyl $R_1$ is especially lower alkyl substituted in the α-position by hydroxy and is, for example, hydroxymethyl, 1-hydroxyethyl, 1-hydroxyprop-1-yl or 2-hydroxyprop-2-yl.

Lower alkanoyloxymethoxycarbonyl is, for example, acetoxymethoxycarbonyl or pivaloyloxymethoxycarbonyl.

α-amino-lower alkanoyloxymethoxycarbonyl is, for example, glycyloxymethoxycarbonyl, valyloxymethoxycarbonyl or leucyloxymethoxycarbonyl.

1-lower alkoxycarbonyloxy-lower alkoxycarbonyl is, for example, ethoxycarbonyloxymethoxycarbonyl or 1-ethoxycarbonyloxyethoxycarbonyl.

1-lower alkoxy-lower alkoxycarbonyl is, for example, methoxymethoxycarbonyl or 1-methoxyethoxycarbonyl.

A 2-oxo-1,3-dioxolen-4-ylmethoxy group that is optionally substituted in the 5-position of the dioxolene ring by lower alkyl or phenyl is especially a 5-phenyl- and more especially a 5-methyl-2-oxo-1,3-dioxolen-4-ylmethoxy group.

Lower alkoxy is, for example, methoxy, also ethoxy, n-propoxy, isopropoxy, n-butoxy, isobutoxy or tert.-butoxy, as well as n-pentyloxy, n-hexyloxy or n-heptyloxy, whilst amino-lower alkoxy is especially 2- or 3-amino-lower alkoxy, such as 2-aminoethoxy or 2-aminopropoxy.

Lower alkanoyloxy is, for example, acetoxy or propionyloxy.

Halogen is, for example, fluorine, chlorine, bromine or iodine.

Lower alkylthio is, for example, methylthio, ethylthio or n-propylthio, whilst amino-lower alkylthio is especially 2- or 3-amino-lower alkylthio, for example 2-aminoethylthio.

Lower alkyl is, for example, methyl, ethyl, n-propyl, isopropyl, n-butyl, isobutyl, sec.-butyl or tert.-butyl, and also n-pentyl, n-hexyl or n-heptyl.

Hydroxy-lower alkyl is, for example, hydroxymethyl, 2-hydroxyethyl or 2,3-dihydroxypropyl.

Lower alkanoyloxy-lower alkyl is, for example, acetoxymethyl or 2-acetoxyethyl.

Carboxy-lower alkyl is, for example, carboxymethyl, 1-carboxy-, 2-carboxy- or 1,2-dicarboxy-ethyl.

Lower alkoxycarbonyl-lower alkyl is, for example, corresponding methyl or ethyl, such as methoxycarbonyl- or ethoxycarbonyl-methyl or 2-methoxycarbonylethyl.

Lower alkoxycarbonyl-lower alkyl substituted by cyano or amino is, for example, lower alkoxycarbonyl-lower alkyl correspondingly substituted in the 2- or 3-position, for example 2-aminoethoxycarbonylmethyl or 2-aminoethoxycarbonylethyl and 2-cyanoethoxycarbonylmethyl or 2-cyanoethoxycarbonylethyl.

Carbamoyl-lower alkyl is, for example, carbamoylmethyl or 2-carbamoylethyl, whilst carbamoyloxy-lower alkyl is, for example, carbamoyloxymethyl or 2-carbamoyloxyethyl.

Cyano-lower alkyl is, for example, cyanomethyl, whilst halo-lower alkyl is, for example, chloromethyl, bromomethyl, 2-chloroethyl or 2,2-dichloroethyl.

Amino-lower alkyl is, for example, aminomethyl or 2-aminoethyl, whilst lower alkylamino-lower alkyl is, for example, methylaminomethyl, ethylaminomethyl, 2-methylaminoethyl or 2-ethylaminoethyl, and di-lower alkylamino-lower alkyl is, for example, dimethylaminomethyl, 2-dimethylaminoethyl or 2-diethylaminoethyl.

Lower alkanoylamino-lower alkyl is, for example, acetaminomethyl, 2-acetaminoethyl or formylaminomethyl.

Amino-carboxy-lower alkyl is, for example, 2-amino-2-carboxyethyl or 1-amino-1-carboxymethyl.

Sulpho-lower alkyl is, for example, sulphomethyl or 2-sulphoethyl.

Lower alkylamino is, for example, methylamino, ethylamino, n-propylamino, isopropylamino or n-butylethylamino, whilst di-lower alkylamino is, for example, dimethylamino, diethylamino, di-n-propylamino or diisopropylamino.

Lower alkanoylamino is, for example, formylamino, acetylamino or propionylamino.

Lower alkoxycarbonyl is, for example, methoxycarbonyl or ethoxycarbonyl.

Lower alkoxycarbonyl substituted by cyano or amino is especially lower alkoxycarbonyl correspondingly substituted in the 2- or 3-position, for example 2-cyanoethoxycarbonyl or 2-aminoethoxycarbonyl.

Preferred as radical $R_1$ is hydroxymethyl and especially 1-hydroxyethyl.

Preferred as radical $R_2$ are carboxy and esterified carboxy cleavable under physiological conditions, for example lower alkanoyloxymethoxycarbonyl, such as acetoxymethoxycarbonyl or pivaloyloxymethoxycarbonyl, and 1-lower alkoxycarbonyloxy-lower alkoxycarbonyl, such as 1-ethoxycarbonyloxyethoxycarbonyl.

Preferred radicals $R_3$ are 3-pyridyl and 3-pyridyl substituted by hydroxy, lower alkoxy, amino-lower alkoxy, halogen, lower alkyl, hydroxy-lower alkyl, carbamoyloxy-lower alkyl, carboxy-lower alkyl, lower alkoxycarbonyl-lower alkyl, carbamoyl-lower alkyl, amino-lower alkyl, cyano-lower alkyl, amino, carboxy, lower alkoxycarbonyl or by carbamoyl, for example 6-hydroxypyrid-3-yl, 6-(2-aminoethoxy)-pyrid-3-yl, 2-, 4- or 6-chloropyrid-3-yl, 2-, 4- or 6-methylpyrid-3-yl, 1-carboxymethyl-, 1-carbamoylmethyl- or 1-methyl-3-pyridinio, 6-hydroxymethylpyrid-3-yl, 6-carbamoyloxymethylpyrid-3-yl, 6-aminomethylpyrid-3-yl, 2- or 6-aminopyrid-3-yl, 2-, 4- or 6-carboxypyrid-3-yl, 2-, 4- or 6-methoxycarbonylpyrid-3-yl, or 2-, 4- or 6-carbamoylpyrid-3-yl, also 4-pyridyl or 4-pyridyl substituted by hydroxy, halogen, lower alkyl, carbamoyloxy-lower alkyl or by carbamoyl, for example 2,6-dichloropyrid-4-yl or 1-methyl-4-pyridinio.

The functional groups present in the compounds of the formula I, such as hydroxy, carboxy or amino groups, especially the hydroxy group in the radical $R_1$ and the carboxy group $R_2$, are optionally protected by protecting groups used in penem, penicillin, cephalosporin and peptide chemistry. Such protecting groups protect the functional groups concerned from undesired condensation reactions, substitution reactions and the like during the synthesis of the compound of the formula I from its precursors.

Such protecting groups can be removed readily, that is to say without undesirable secondary reactions taking place, for example by solvolysis or reduction.

Protecting groups of this type and the methods by which they are introduced and removed are described, for example, in J. F. W. McOmie, 'Protective Groups in Organic Chemistry', Plenum Press, London, N.Y., 1973, T. W. Greene, 'Protective Groups in Organic Synthesis', Wiley, N.Y., 1981, 'The Peptides', Vol. I, Schroeder and Luebke, Academic Press, London, N.Y., 1965, and Houben-Weyl, 'Methoden der Organischen Chemie', Vol. 15/1, Georg Thieme Verlag, Stuttgart, 1974.

In compounds of the formula (I), a hydroxy group in the radical $R_1$ and also a hydroxy group present in the radical $R_3$ may be protected, for example, by acyl radicals. Suitable acyl radicals are, for example, lower alkanoyl optionally substituted by halogen, for example acetyl, dichloroacetyl or trifluoroacetyl, benzoyl optionally substituted by nitro, for example benzoyl, 4-nitrobenzoyl or 2,4-dinitrobenzoyl, lower alkoxycarbonyl optionally substituted by halogen, for example 2-bromoethoxycarbonyl or 2,2,2-trichloroethoxycarbonyl, lower alkenyloxycarbonyl, for example allyloxycarbonyl, lower alkenyloxyoxalyl, for example allyloxyoxalyl, or phenyl-lower alkoxycarbonyl optionally substituted by nitro, for example benzyloxycarbonyl or 4-nitrobenzyloxycarbonyl. Further suitable hydroxy-protecting groups are, for example, trisubstituted silyl, such as tri-lower alkylsilyl, for example trimethylsilyl, dimethyl-(2,3-dimethylbut-2-yl)silyl or tert.-butyldimethylsilyl, and 2-oxa- or 2-thia-cycloalkyl having from 5 to 7 carbon atoms, for example 2-tetrahydropyranyl or 2-tetrahydrofuranyl. Tri-lower alkylsilyl, lower alkenyloxyoxalyl and lower alkenyloxycarbonyl are preferred as hydroxy-protecting groups.

A carboxy group $R_2$ and also a carboxy group present in the radical $R_3$ is customarily protected in esterified form, the ester group being readily cleavable under mild conditions, for example under mildly reductive, such as hydrogenolytic, conditions, or under mildly solvolytic, such as acidolytic or especially basic- or neutral-hydrolytic, conditions. Such esterified carboxy groups contain as esterifying groups especially lower alkyl groups that are branched in the 1-position or suitably substituted in the 1- or 2-position. Suitable carboxy groups in esterified form are, inter alia, benzyloxycarbonyl optionally substituted by nitro or lower alkoxy, such as methoxy, for example 4-nitrobenzyloxycarbonyl or 4-methoxybenzyloxycarbonyl, lower alkanoylmethoxycarbonyl, such as acetonyloxycarbonyl, benzoylmethoxycarbonyl in which the benzoyl group is optionally substituted, for example, by halogen, such as bromine, for example phenacyloxycarbonyl, halo-lower alkoxycarbonyl, such as 2-halo-lower alkoxycarbonyl, for example 2,2,2-trichloroethoxycarbonyl or 2-bromoethoxycarbonyl, lower alkenyloxycarbonyl, for example allyloxycarbonyl, or ethoxycarbonyl substituted in the 2-position by lower alkylsulphonyl, cyano or by trisubstituted silyl, such as tri-lower alkylsilyl or triphenylsilyl, for example 2-methylsulphonylethoxycarbonyl, 2-cyanoethoxycarbonyl, 2-trimethylsilylethoxycarbonyl or 2-(di-n-butylmethylsilyl)-ethoxycarbonyl. Preferred protected carboxy groups are the 4-nitrobenzyloxycarbonyl and lower alkenyloxycarbonyl, especially allyloxycarbonyl, groups, and the ethoxycarbonyl group substituted in the 2-position by tri-lower alkylsilyl, for example trimethylsilyl or di-n-butylmethylsilyl.

A protected amino group in the radical $R_3$ can be, for example, in the form of a readily cleavable acylamino group or in the form of an azido group. In a corresponding acylamino group, acyl is, for example, the acyl radical of an organic acid having, for example, up to 12 carbon atoms, especially a lower alkanecarboxylic acid optionally substituted, for example, by halogen orphenyl, or especially of a carbonic acid semiester. Such acyl groups are, for example, halo-lower alkanoyl, such as 2-haloacetyl, especially 2,2,2-trifluoro- or 2,2,2-trichloro-acetyl, lower alkenyloxycarbonyl, for example allyloxycarbonyl, lower alkoxycarbonyl optionally substituted in the 1- or 2-position, such as lower alkoxycarbonyl, for example tert.-butoxycarbonyl, optionally substituted benzyloxycarbonyl, for example 4-nitrobenzyloxycarbonyl, 2-halo-lower alkoxycarbonyl, for example 2,2,2-trichloroethoxycarbonyl or 2-bromoethoxycarbonyl, or 2-(trisubstituted silyl)ethoxycarbonyl, such as 2-tri-lower alkylsilylethoxycarbonyl, for example 2-trimethylsilylethoxycarbonyl or 2-(di-n-butylmethylsilyl)-ethoxycarbonyl. Preferred protected amino groups are azido, lower alkenyloxycarbonylamino, for example allyloxycarbonylamino, and benzyloxycarbonylamino optionally substituted by nitro.

A monosubstituted amino group, for example lower alkylamino, is protected in the same manner as an amino group, for example in the form of substituted lower alkenyloxycarbonylamino.

A protected sulpho group in the radical $R_3$ is protected in the same manner as a protected carboxy group, especially in esterified form.

Salts of compounds according to the invention are especially pharmaceutically acceptable, non-toxic salts of compounds of the formula I. Such salts are formed, for example, from the acidic groups present in compounds of the formula I, for example carboxy groups, and are especially metal or ammonium salts, such as alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis-(2-hydroxyethyl)-amine, tris-(2-hydroxyethyl)-amine or 2-amino-1,3-dihydroxymethylpropane ("Tris"), basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or N-benzyl-β-phenethylamine. Compounds of the formula I having a basic group, for example having an amino group, can form acid addition salts, for example with inorganic acids, such as hydrochloric acid, sulphuric acid or phosphoric acid, or with suitable organic carboxylic or sulphonic acids, for example acetic acid, succinic acid, fumaric acid, maleic acid, tartaric acid, oxalic acid, citric acid, benzoic acid, mandelic acid, malic acid, ascorbic acid, methanesulphonic acid or 4-toluenesulphonic acid. Compounds of the formula I having an acidic group and a basic group can also be in the form of internal salts, that is to say in zwitterionic form. For example, compounds of the formula I having a pyridinio group $R_3$ can be in carboxylate form ($R_2$ is $COO^\ominus$).

For the purposes of isolation or purification it is also possible to use pharmaceutically unsuitable salts. Only the pharmaceutically acceptable, non-toxic salts are used therapeutically, and these are therefore preferred.

The penem compounds of the formula I can have an additional chiral centre in the radical $R_1$. For example, 1-hydroxyethyl as a substituent $R_1$ can be in the R-, the S- or in the racemic R,S-configuration. In preferred penem compounds of the formula I, a radical $R_1$ having an asymmetric carbon atom, especially 1-hydroxyethyl, has the R-configuration. The invention accordingly relates to the pure diastereoisomers and mixtures of diastereoisomers of compounds of the formula I that have an additional chiral centre in the radical $R_1$.

The compounds of the formula I have valuable pharmacological properties or can be used as intermediates for the manufacture of such compounds having valuable pharmacological properties. Compounds of the formula I in which $R_1$ represents lower alkyl substituted by hydroxy, $R_3$ has the meanings given under formula I, functional groups being in unprotected form, and $R_2$ represents carboxy or an esterified carboxy group that can be cleaved under physiological conditions, and pharmacologically acceptable salts of such compounds having salt-forming groups have antibacterial activity. For example, they are effective in vitro against gram-positive and gram-negative cocci, for example staphylococci (including methicillin-resistant staphylococci), such as *Staphylococcus aureus, Streptococcus pyogenes, Streptococcus pneumoniae, Streptococcus faecalis* and *Neisseria* spec., in minimum concentrations of from <0.01 to approximately 8 μg/ml, and against gram-negative rod-shaped bacteria, such as *Enterobacteriaceae* and *Haemophilus influenzae, Pseudomonas* and anaerobes, for example *Bacteroides* sp., in minimum concentrations of from approximately 0.02 to approximately 64 μg/ml. In vivo, in the systemic infection of mice, for example by *Staphylococcus aureus*, in the case of parenteral or oral administration of compounds according to the invention $ED_{50}$ values of from approximately 0.5 to approximately 15 mg/kg are obtained.

The novel compounds can be used as orally or parenterally administrable antibacterial broad spectrum antibiotics, for example in the form of corresponding pharmaceutical preparations, for the treatment of infections.

Compounds of the formula I in which at least one of the functional groups present is in protected form can be used as intermediates in the manufacture of the above-mentioned pharmacologically active compounds of the formula I.

The invention relates especially to compounds of the formula I in which $R_1$ represents lower alkyl substituted by hydroxy or by protected hydroxy; $R_2$ represents carboxy, esterified carboxy that can be cleaved under physiological conditions, or protected carboxy $R_2'$; and $R_3$ represents 3-pyridyl, 4-pyridyl, or 3- or 4-pyridyl substituted by hydroxy, lower alkoxy, amino-lower alkoxy, lower alkanoyloxy, halogen, mercapto, lower alkylthio, amino-lower alkylthio, phenylthio, lower alkyl, hydroxy-lower alkyl, lower alkanoyloxy-lower alkyl, carboxy-lower alkyl, lower alkoxycarbonyl-lower alkyl, cyano- or amino-substituted lower alkoxycarbonyl-lower alkyl, carbamoyl-lower alkyl, carbamoyloxy-lower alkyl, cyano-lower alkyl, halo-lower alkyl, amino-lower alkyl, lower alkylamino-lower alkyl, di-lower alkylamino-lower alkyl, lower alkanoylamino-lower alkyl, amino-carboxy-lower alkyl, sulpho-lower alkyl, amino, lower alkylamino, di-lower alkylamino, lower alkanoylamino, carboxy, lower alkoxycarbonyl, cyano- or amino-substituted lower alkoxycarbonyl, carbamoyl, cyano, sulpho, sulphamoyl, oxido and/or by optionally lower alkyl-, lower alkoxy- and/or halo-substituted phenyl, and salts of compounds of the formula I.

The invention relates more especially to compounds of the formula I in which $R_1$ represents hydroxymethyl or 1-hydroxyethyl, $R_2$ represents carboxy or esterified carboxy that can be cleaved under physiological conditions, and $R_3$ represents 3-pyridyl, 3-pyridyl substituted by hydroxy, lower alkoxy, amino-lower alkoxy, halogen, lower alkyl, hydroxy-lower alkyl, carboxy-lower alkyl, lower alkoxycarbonyl-lower alkyl, carbamoyloxy-lower alkyl, carbamoyl-lower alkyl, amino-lower alkyl, cyano-lower alkyl, amino, carboxy, lower alkoxycarbonyl or by carbamoyl, or 4-pyridyl, or 4-pyridyl substituted by hydroxy, halogen, lower alkyl, carbamoyloxy-lower alkyl or by carbamoyl, and salts of compounds of the formula I.

The invention relates especially to compounds of the formula I in which $R_1$ represents hydroxymethyl or 1-hydroxyethyl, $R_2$ represents carboxy or esterified carboxy that can be cleaved under physiological conditions, and $R_3$ represents 3-pyridyl or 3-pyridyl substituted by lower alkyl or by halogen, and salts of compounds of the formula I.

The invention relates especially to the compounds of the formula I mentioned in the Examples and to their salts, especially their pharmaceutically acceptable salts.

The compounds of the present invention can be manufactured by processes known per se.

The novel compounds are manufactured, for example, as follows:

an ylide compound of the formula

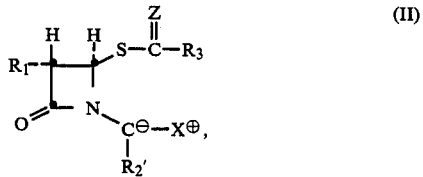

(II)

in which $R_1$ and $R_3$ have the meanings given under formula I, $R_2'$ represents a protected carboxy group, Z represents oxygen or sulphur and $X^\oplus$ represents either a trisubstituted phosphonio group or a diesterified phosphono group together with a cation, is cyclised, or a compound of the formula

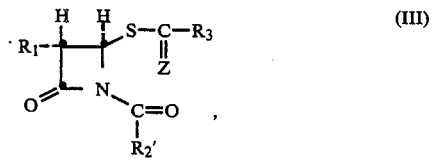

(III)

in which R and $R_3$ have the meanings given under formula I and $R_2'$ and Z have the meanings given under formula II, is treated with an organic compound of trivalent phosphorus, and, if desired or necessary, in a resulting compound of the formula I protected functional groups are converted into the free functional groups, and/or, if desired, in a resulting compound of the formula I a free carboxy group $R_2$ is converted into an esterified carboxy group $R_2$ that can be cleaved under physiological conditions, and/or, if desired, in a resulting compound of the formula I a radical $R_3$ is converted into a different radical $R_3$, and/or, if desired, a resulting compound having a salt-forming group is converted into a salt, or a resulting salt is converted into the free compound or into a different salt.

In the starting compounds of the formulae II and III, functional groups, such as a free hydroxy group in the radical $R_1$ and other functional groups contained in the radical $R_3$, are preferably protected by conventional protecting groups, for example by those mentioned above.

Cyclisation of the compound of the formula II

The group $X^\oplus$ in a starting material of the formula II is one of the phosphonio or phosphono groups customarily used in Wittig condensation reactions, especially a triaryl-, for example triphenyl-, or tri-lower alkyl-, for example tri-n-butyl-, phosphonio group, or a phosphono group diesterified by lower alkyl, for example ethyl, the symbol $X^\oplus$ in the case of the phosphono group including in addition the cation of a strong base, especially a suitable metal ion, such as an alkali metal ion, for example a lithium, sodium or potassium ion. Preferred as the group $X^\oplus$ is, on the one hand, triphenylphosphonio and, on the other hand, diethylphosphono together with an alkali metal ion, for example a sodium ion.

Cyclisation may take place spontaneously, that is to say during the manufacture of the starting materials, or may be effected by heating, for example in a temperature range of approximately from 30° C. to 160° C., preferably from approximately 80° C. to approximately 120° C. The reaction is preferably carried out in a suitable inert solvent, such as an aliphatic, cycloaliphatic or aromatic hydrocarbon, for example cyclohexane, benzene or toluene, a halogenated hydrocarbon, for example methylene chloride, an ether, for example diethyl ether, a cyclic ether, for example dioxan or tetrahydrofuran, a carboxylic acid amide, a di-lower alkyl sulphoxide or a lower alkanol, or in a mixture thereof, and, if necessary, in an inert gas atmosphere, for example a nitrogen atmosphere.

Cyclisation of the compound of the formula III

An organic compound of trivalent phosphorus is derived, for example, from phosphorous acid and is especially an ester thereof with a lower alkanol, for example methanol or ethanol, and/or with an optionally substituted aromatic hydroxy compound, for example phenol or pyrocatechol, or is an amide ester thereof of the formula $P(OR_a)_2N(R_b)_2$ in which each of $R_a$ and $R_b$, independently of the other, represents lower alkyl, for example methyl, or aryl, for example phenyl. Preferred compounds of trivalent phosphorus are tri-lower alkyl phosphites, for example trimethyl phosphite or triethyl phosphite.

The reaction is preferably carried out in an inert solvent, such as an aromatic hydrocarbon, for example benzene or toluene, an ether, for example dioxan or tetrahydrofuran, or a halogenated hydrocarbon, for example methylene chloride or chloroform, at a temperature of approximately from 20° to 140° C., preferably from approximately 80° to approximately 120° C., one molar equivalent of a compound of the formula III being reacted with at least two molar equivalents of the phosphorus compound. For example, the compound of the formula III is placed in an inert solvent and the phosphorus compound, preferably dissolved in the same inert solvent, is added dropwise thereto over a relatively long period, for example over a period of from 2 to 4 hours.

In a preferred form of the process, the starting material of the formula III is manufactured as indicated below and, without being isolated from the reaction mixture, is reacted with the organic compound of trivalent phosphorus, the end products of the formula I being formed.

Compounds of the formula I obtainable according to the process can be converted in a manner known per se into other compounds of the formula I.

For example, in a resulting compound of the formula I in which one or more functional groups are protected, these groups, for example protected carboxy, hydroxy and/or amino groups, may be freed, optionally in stages or simultaneously, in a manner known per se by means of solvolysis, especially hydrolysis, alcoholysis or acidolysis, or by means of reduction, especially hydrogenolysis or chemical reduction.

In a compound of the formula I obtainable according to the process in which $R_2$ represents a protected carboxy group and/or in which the radical $R_3$ contains protected carboxy as substituent, the protected carboxy group can be freed in a manner known per se. Thus, ethoxycarbonyl substituted in the 2-position by a trisubstituted silyl group can be converted into free carboxy, for example, by treatment with a carboxylic acid, such as formic acid or trifluoroacetic acid, optionally with the addition of a nucleophilic compound, such as phenol or anisole. Optionally substituted benzyloxycarbonyl can be cleaved, for example, by means of hydrogenolysis, that is to say by treatment with hydrogen in the presence of a metallic hydrogenation catalyst, such as a palladium catalyst. Furthermore, suitably substituted benzyloxycarbonyl, such as 4-nitrobenzyloxycarbonyl, can also be converted into free carboxy by means of chemical reduction, for example by treatment with an alkali metal dithionite, for example sodium dithionite, or with a reducing metal, for example tin, customarily in the presence of a hydrogen-yielding agent that together with the metal is capable of producing nascent hydrogen, such as a suitable carboxylic acid, for example a lower alkanecarboxylic acid optionally substituted, for example, by hydroxy, for example acetic acid, or in the presence of an alcohol or thiol, it being preferable to add water. The removal of an allyl protecting group can be effected, for example, by reaction with a palladium compound, for example tetrakis(triphenylphosphine)palladium, optionally in the presence of triphenylphosphine and with the addition of an allyl group acceptor, such as a carboxylic acid, for example 2-ethylhexanoic acid, or a salt thereof, or tributyltin hydride or dimedone. By treatment with a reducing metal or metal salt, as described above, it is also possible to convert 2-halo-lower alkoxycarbonyl (optionally after converting a 2-bromo-lower alkoxycarbonyl group into a corresponding 2-iodo-lower alkoxycarbonyl group) or benzoylmethoxycarbonyl into free carboxy, it being possible to cleave benzoylmethoxycarbonyl also by treatment with a nucleophilic, preferably salt-forming, reagent, such as sodium thiophenolate or sodium iodide. Substituted 2-silylethoxycarbonyl can be converted into free carboxy also by treatment with a salt of hydrofluoric acid that yields the fluoride anion, such as an alkali metal fluoride, for example sodium fluoride, in the presence of a macrocyclic polyether ("Crown ether") or with a fluoride of an organic quaternary base, such as tetra-lower alkylammonium fluoride, for example tetrabutylammonium fluoride. A lower alkoxycarbonyl group substituted in the 2-position by lower alkylsulphonyl or cyano can be converted into free carboxy, for example, by treatment with a basic agent, such as an alkali metal or alkaline earth metal hydroxide or carbonate, for example sodium or potassium hydroxide or sodium or potassium carbonate.

As a further possibility, compounds of the formula I in which $R_2$ represents carboxy can be converted into compounds of the formula I in which $R_2$ represents an esterified carboxy group that can be cleaved under physiological conditions. Such esters can be manufactured, for example, by reaction of a salt of the acid, which salt is optionally produced in situ, with a reactive ester of a corresponding alcohol and a strong inorganic acid, such as sulphuric acid, or a strong organic sulphonic acid, such as 4-toluenesulphonic acid. Furthermore, in compounds of the formula I that contain a carboxy group protected in esterified form, the carboxy-protecting group can be removed as described above, and a resulting compound of the formula I having a free carboxy group, or a salt thereof, can be converted by reaction with the reactive ester of a corresponding alcohol into a compound of the formula I in which $R_2$ represents an esterified carboxy group that can be cleaved under physiological conditions.

In compounds of the formula I obtainable according to the process in which the radical $R_1$ and/or the radical $R_3$ contains protected hydroxy as substituent, the protected hydroxy group can be converted into the free hydroxy group in a manner known per se. For example, a hydroxy group protected by a suitable acyl group or by an organic silyl group is freed in the same manner as a correspondingly protected amino group (see below); for example, a tri-lower alkylsilyl group may be removed also with tetrabutylammonium fluoride and acetic acid (under these conditions, carboxy groups protected by tri-substituted silylethoxy are not cleaved).

In a compound of the formula I obtainable according to the invention having a protected amino group in the radical $R_3$, this group may be converted into the free amino group in a manner known per se, for example, depending on the nature of the protecting group, preferably by means of solvolysis or reduction. For example, 2-halo-lower alkoxycarbonylamino (optionally after converting a 2-bromo-lower alkoxycarbonylamino group into a 2-iodo-lower alkoxycarbonylamino group) and 4-nitrobenzyloxycarbonylamino can be cleaved by treatment with a suitable chemical reducing agent, such as zinc in the presence of a suitable carboxylic acid, such as aqueous acetic acid, or by catalysis with hydrogen in the presence of a palladium catalyst, or by treatment with an alkali metal dithionite, for example sodium dithionite. Optionally substituted benzyloxycarbonylamino may be cleaved, for example, by means of hydrogenolysis, that is to say by treatment with hydrogen in the presence of a suitable hydrogenation catalyst, such as a palladium catalyst, and allyloxycarbonylamino may be cleaved by reaction with a palladium compound, for example tetrakis(triphenylphosphine)palladium, optionally in the presence of triphenylphosphine and in the presence of an allyl group acceptor, such as a carboxylic acid, for example 2-ethylhexanoic acid, or a salt thereof, or tributyltin hydride or dimedone. An amino group protected by 2-halo-lower alkanoyl, for example 2-chloroacetyl, can be freed by treatment with thiourea in the presence of a base or with a salt, such as an alkali metal salt, of thiourea and subsequent solvolysis, such as alcoholysis or hydrolysis, of the resulting condensation product. An amino group protected by 2-substituted silylethoxycarbonyl can be converted into the free amino group by treatment with a salt of hydrofluoric acid that yields fluoride anions, such as an alkali metal fluoride, for example sodium fluoride, in the presence of a macrocyclic polyether ("Crown ether") or with a fluoride of an organic quaternary base, such as tetra-lower alkylammonium fluoride, for example tetraethylammonium fluoride. An amino group protected in the form of an azido group is converted into free amino, for example, by reduction, for example by catalytic hydrogenation with hydrogen in the presence of a hydrogenation catalyst, such as platinum oxide or palladium, or by treatment with zinc in the presence of an acid, such as acetic acid.

In compounds of the formula I it is also possible to convert a radical $R_3$ into a different radical $R_3$.

Thus, for example, in compounds of the formula I in which the radical $R_3$ is substituted by a carboxy group, this carboxy group can be converted according to processes known per se into a functionally modified carboxy group, such as into an esterified carboxy group or into carbamoyl. For example, by reacting a compound of the formula I in which the radical $R_3$ is substituted by carboxy with an optionally substituted lower alkanol there is obtained a compound of the formula I in which $R_3$ is substituted by optionally substituted lower alkoxycarbonyl, it being preferable to carry out the operation in the presence of a suitable condensation agent, for example a carbodiimide, or to remove by azeotropic distillation the water that is formed. On the other hand, carboxy groups in radicals $R_3$ can also be converted into reactive functional derivatives, such as mixed anhydrides, for example acid halides, or activated esters, and these can be converted by reaction with a corresponding alcohol, for example an optionally substituted lower alkanol, or with ammonia into correspondingly esterified carboxy groups or into carbamoyl groups, it being preferable when using mixed anhydrides to carry out the operation in the presence of an acid-binding agent, such as an aromatic or tertiary amine or an alkali metal or alkaline earth metal carbonate.

In compounds of the formula I in which the radical $R_3$ is substituted by amino, the amino group may be converted into a substituted amino group, for example a lower alkylamino, di-lower alkylamino or lower alkanoylamino group. The conversion into a lower alkylamino or di-lower alkylamino group is effected, for example, by reaction with a reactive esterified lower alkanol, for example with a lower alkyl halide or sulphonate, in the presence of a basic condensation agent, such as a hydroxide or carbonate of an alkali metal or alkaline earth metal or a heteroaromatic nitrogen base, for example pyridine. In analogous manner, amino can be converted by treatment with the reactive functional derivative of a lower alkanecarboxylic acid, for example the corresponding carboxylic acid halide, into lower alkanoylamino. Compounds of the formula I having an unsubstituted pyridine nitrogen atom in the radical $R_3$ can also be converted by reaction with the reactive esters of an optionally substituted lower alkanol, for example a benzenesulphonate, p-toluenesulphonate, methanesulphonate or halide, for example chloride, thereof, into compounds of the formula I in which $R_3$ is a pyridyl radical substituted at the nitrogen atom by optionally substituted lower alkyl.

Salts of compounds of the formula I having salt-forming groups can be manufactured in a manner known per se. Thus, salts of compounds of the formula I having a free carboxy or sulpho group can be formed, for example, by treatment with metal compounds, such as alkali metal salts of suitable organic carboxylic acids, for example the sodium salt of α-ethylcaproic acid, or with inorganic alkali metal or alkaline earth metal salts, for example sodium hydrogen carbonate, or with ammonia or with a suitable organic amine, it being preferable to use stoichiometric amounts or only a small excess of the salt-forming agent. Acid addition salts of compounds of the formula I are obtained in customary manner, for example by treatment with a suitable acid or a suitable anion exchange reagent. Internal salts of compounds of the formula I can be formed, for example, by neutralising salts, such as acid addition salts, to the isoelectric point, for example with weak bases, or by treatment with ion exchangers.

Salts can be converted into the free compounds in customary manner; metal and ammonium salts, for example, by treatment with suitable acids, and acid addition salts, for example, by treatment with a suitable basic agent.

Resulting mixtures of isomeric compounds can be separated into the individual isomers in a manner known per se. Mixtures of diastereoisomeric compounds can be separated, for example, by fractional crystallisation. Resulting racemates can be reacted, for example, with an optically active auxiliary, the resulting mixture of two diastereoisomeric compounds can be separated by fractional crystallisation and the individual diastereoisomers can be cleaved to form the optically active compounds.

In all subsequent conversions of resulting compounds of the formula I, those reactions are preferred which take place under moderately alkaline or, especially, neutral conditions.

The process also includes those forms according to which compounds formed as intermediates are used as starting materials and the remaining process steps are carried out with them, or the process is discontinued at any stage. Furthermore, starting materials can be used in the form of derivatives or can be formed in situ, optionally under the reaction conditions.

The starting compounds of the formulae II and III can be manufactured as indicated in the following reaction scheme I:

Reaction scheme I

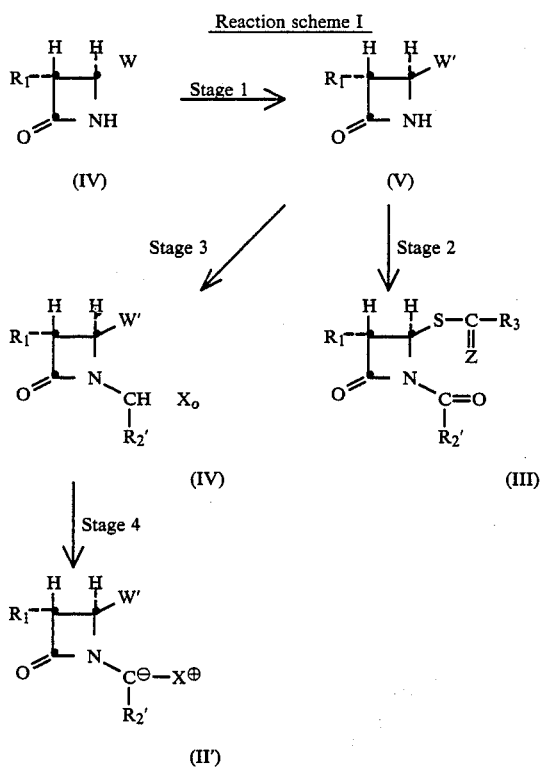

In the compounds of the formulae V, VI and II', W' represents the radical —S—C(=Z)—R$_3$ or triphenylmethylthio or lower alkanoylthio.

Stage 1

Suitable starting compounds of the formula IV in which W represents a radical that can readily be exchanged by nucleophilic reaction, for example lower alkanoyloxy, such as acetoxy, or sulphonyloxy R$_o$—SO$_2$— in which R$_o$ represents, for example, optionally hydroxy-substituted lower alkyl, such as methyl, tert.-butyl or 2-hydroxyethyl, are known, for example, from the published European Patent Application No. 82113, German Offenlegungsschrift No. 3 224 055 and German Offenlegungsschrift No. 3 013 997 or can be manufactured in a manner analogous thereto.

A compound that introduces the radical —S—C(=Z)—R$_3$ is, for example, an acid of the formula R$_3$—C(=Z)—SH or especially a salt thereof, for example an alkali metal salt, such as the sodium or potassium salt. The substitution may be carried out in an organic solvent, such as in a lower alkanol, a lower alkanecarboxylic acid amide, a cyclic ether, or in a similar inert solvent, at room temperature or at slightly elevated or reduced temperature, for example at from approximately 0° to approximately 40° C. The introduction of a triphenylmethylthio or lower alkanoylthio radical W' is effected in an analogous manner by reaction with an alkali metal salt, for example the sodium salt, of a thio-lower alkanecarboxylic acid, for example thioacetic acid, or of triphenylmethyl mercaptan.

Stage 2

A starting compound of the formula III is obtained by treating an azetidinone of the formula V in which W' represents the radical —S—C(=Z)—R$_3$ with an acid of the formula R$_2'$—COOH or especially with a reactive derivative, such as an ester or acid halide, for example the acid chloride, thereof, at a temperature of from −50° to 80° C., preferably at from −20° to 0° C., in an inert solvent, such as one of those mentioned for the reaction of compounds of the formula III to form compounds of the formula I. When using an acid halide, the operation is preferably carried out in the presence of an acid-binding agent, such as a tertiary aliphatic amine, an aromatic amine, or especially an alkali metal or alkaline earth metal carbonate or hydrogen carbonate.

Compounds of the formula V in which W' represents triphenylmethylthio or lower alkanoylthio can be converted into the starting compounds of the formula V in which W' represents the radical —S—C(=Z)-R$_3$ by reacting them in the presence of a base, for example pyridine or tri-n-butylamine, in a suitable solvent, for example diethyl ether or methanol, with a salt of the formula MA in which M represents a transition metal cation, especially the silver cation, and A represents a customary anion that promotes the solubility of the salt MA in the chosen solvent, for example the nitrate, acetate or fluoride anion, and treating the resulting salt of the formula

with an acylating agent that introduces the radical R$_3$—C(=Z)—, for example with the acid R$_3$—C(=Z)—OH or with a reactive functional derivative, such as an acid halide, for example the chloride or bromide, azide or anhydride, thereof. If a reactive functional derivative of the acid of the formula R$_3$—C(=Z)—OH, for example the acid chloride, is used, the acylation is effected in an inert solvent, such as a chlorinated hydrocarbon, or an ether, at room temperature or while heating or cooling, for example in a temperature range of from approximately −50° to approximately +60° C., especially at from approximately −30° to approximately +20° C.

Stage 3

Compounds of the formula VI in which X$_o$ represents a reactive esterified hydroxy group, especially halogen, for example chlorine or bromine, are manufactured by reacting a compound of the formula V with a glyoxylic acid compound of the formula R$_2'$—CHO or a suitable derivative thereof, such as a hydrate, hemihydrate or hemiacetal, for example a hemiacetal with a lower alkanol, for example methanol or ethanol, and in a resulting compound of the formula VI in which X$_o$ represents hydroxy, converting the hydroxy group into a reactive esterified hydoxy group. The compounds of the formula VI are customarily obtained in the form of a mixture of the two isomers [with respect to the grouping —CH(R$'_2$) X$_o$].

The addition of the glyoxylic acid ester compound to the nitrogen atom of the lactam ring in the compound of the formula V takes place at room temperature or, if necessary, while heating. When using the hydrate of the glyoxylic acid compound, water is formed which, if necessary, is removed by distillation, for example azeotropic distillation, or by using a suitable dehydrating agent. The operation is preferably carried out in the presence of a suitable inert solvent or solvent mixture.

The conversion of a hydroxy group $X_o$ into a reactive esterified hydroxy group $X_o$ in a compound of the formula VI is carried out by treatment with a suitable esterifying agent, for example with a thionyl halide, for example thionyl chloride, preferably in the presence of a basic, especially organic basic, agent, such as an aliphatic tertiary amine, or in the presence of a heterocyclic base of the pyridine type. Preferably, the operation is carried out in the presence of a suitable solvent, for example dioxan or tetrahydrofuran, or a solvent mixture, if necessary while cooling, for example at from approximately $-30°$ to approximately $30°$ C.

Stage 4

The starting material of the formula II is obtained by treating a compound of the formula VI with a suitable phosphine compound, such as a tri-lower alkylphosphine, for example tri-n-butylphosphine, or a triarylphosphine, for example triphenylphosphine, or with a suitable phosphite compound, such as a tri-lower alkyl phosphite, for example triethyl phosphite, or an alkali metal di-lower alkyl phosphite, for example an alkali metal diethyl phosphite, and converting a resulting compound of the formula II' in which W" represents triphenylmethylthio or lower alkanoylthio into a compound of the formula II' in which W' represents the radical $-S-C(=Z)-R_3$.

The reaction with the phosphine or phosphite compound is preferably carried out in a suitable inert solvent, such as a hydrocarbon, or an ether, or in a solvent mixture. Depending on the reactivity, the operation is carried out while cooling or at elevated temperature, for example from $-10°$ to $+100°$ C., preferably at approximately from $20°$ to $80°$ C. The operation is customarily carried out in the presence of a basic agent, such as an organic base, for example an amine, or "polystyrene Hunig base", or an inorganic base, for example an alkali metal carbonate, the initially formed phosphonium compound of the formula

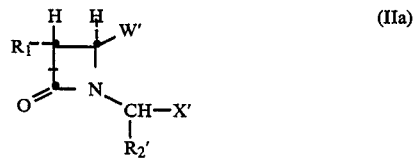

(IIa)

in which X' represents a phosphono group or a phosphonio group together with an anion which, depending on the meaning of the radical $X_o$ (see formula VI), may be, for example, a chloride anion, being converted into the ylide starting material of the formula II.

The introduction of the radical $-S-C(=Z)-R_3$ into compounds of the formula II' in which W' represents lower alkanoylthio or triphenylmethylthio can be effected in a manner analogous to that described in Stage 2.

The process described in Reaction Scheme I for the manufacture of the compounds of the formulae II, III, V and VI, and also the processes given for the manufacture of the end products of the formula I, can also be carried out with optically inactive compounds, and, at any stage of the process, the optically active compounds according to the present invention can be isolated in known manner from a resulting diastereoisomeric mixture or racemate.

The invention relates also to the novel starting compounds and to novel intermediates obtainable according to the process, such as those of the formulae II, III, V and VI (W' represents the radical $-S-C(=Z)-R_3$), and to the processes given for their manufacture.

The starting compounds used and the reaction conditions chosen are preferably those which result in the compounds of the formula I described hereinbefore as being especially preferred.

The pharmacologically acceptable compounds of the present invention can be used, for example, for the manufacture of pharmaceutical preparations that contain a therapeutically effective amount of the active ingredient together or in admixture with inorganic or organic, solid or liquid, pharmaceutically acceptable carriers that are suitable for oral or for parenteral, that is to say, for example, intramuscular, intravenous, subcutaneous or intraperitoneal, administration.

For oral administration there are used tablets or gelatine capsules that contain the active ingredient together with diluents, for example lactose, dextrose, sucrose, mannitol, sorbitol, cellulose and/or glycine, and lubricants, for example silica, talc, stearic acid or salts thereof, such as magnesium or calcium stearate, and/or polyethylene glycol. Tablets also contain binders, for example magnesium aluminium silicate, starches, such as corn, wheat, rice or arrowroot starch, gelatine, tragacanth, methylcellulose, sodium carboxymethylcellulose and/or polyvinylpyrrolidone, and, if desired, disintegrators, for example starches, agar, alginic acid or salts thereof, such as sodium alginate, and/or effervescent mixtures or adsorbents, colourings, flavourings or sweeteners.

For parenteral administration there are suitable especially infusion solutions, preferably isotonic aqueous solutions or suspensions, it being possible to prepare these before use, for example from lyophilised preparations that contain the active ingredient alone or together with a carrier, for example mannitol. Such preparations may be sterilised and/or contain adjuncts, for example preservatives, stabilisers, wetting agents and/or emulsifiers, solubilisers, salts for regulating the osmotic pressure and/or buffers.

The present pharmaceutical preparations, which, if desired, may contain other pharmacologically valuable substances, are manufactured in a manner known per se, for example by means of conventional mixing, dissolving or lyophilising processes, and contain from approximately 0.1 to 100%, especially from approximately 1 to approximately 50% or, in the case of lyophilisates, up to 100%, of the active ingredient.

Depending upon the type of infection and the condition of the infected organism, the daily dose (oral or parenteral) used for the treatment of warm-blooded animals (humans and animals) weighing approximately 70 kg is from approximately 200 mg to approximately 1 g.

The following Examples serve to illustrate the invention. Temperatures are given in degrees Celsius.

Experimental section

EXAMPLE 1

(5R,6S)-2-(3-pyridyl)-6-[(1R)-1-allyloxycarbonyloxyethyl]-2-penem-3-carboxylic acid allyl ester A solution of 3.1 g of 2-[(3S,4R)-3-[(1R)-1-allyloxycarbonyloxyethyl]-4-nicotinoylthio-2-oxoazetidin-1-yl]-2-triphenylphosphoranylideneacetic acid allyl ester in 600 ml of toluene is stirred under an argon atmosphere for 3 hours at reflux temperature. The solvent is then evaporated off and the crude product is purified by chromatography on silica gel (eluant: toluene/ethyl acetate 9:1 to 85:15).

R$_f$(ethyl acetate): 0.5
IR (CH$_2$Cl$_2$): 1795, 1747, 1715, 1575 cm$^{-1}$.

The starting material can be manufactured as follows:

2-[(3S,4R)-3-[(1R)-1-allyloxycarbonyloxyethyl]-4-nicotinoylthio-2-oxo-azetidin-1-yl]-2-triphenylphosphoranylideneacetic acid allyl ester 6.96 g of the silver salt of 2-[(3S,4R)-3-[(1R)-1allyloxycarbonyloxyethyl]-4-mercapto-2-oxo-azetidin-1-yl]-2-triphenylphosphoranylideneacetic acid allyl ester are dissolved in 110 ml of methylene chloride and, at 0°, 3.2 ml of pyridine, 200 mg of 4-dimethylaminopyridine and then 2.68 g of nicotinoyl chloride hydrochloride are added. After stirring for 20 minutes at 0°, the solid is filtered off over Hyflo and the filtrate is washed with aqueous sodium hydrogen carbonate solution and then with saturated sodium chloride solution. After drying over MgSO$_4$, the solvent is evaporated off. The residue is purified by chromatography on silica gel (eluant: toluene/ethyl acetate 9:1 to 3:2).

TLC (ethyl acetate) R$_f$=0.33
IR (CH$_2$Cl$_2$): 1755, 1670, 1645, 1585 cm$^{-1}$.

EXAMPLE 2

Sodium salt of (5R,6S)-2-(3-pyridyl)-6-[(1R)-1-hydroxyethyl]-2-penem-3-carboxylic acid 110 mg of tetrakis(triphenylphosphine)palladium and 1.6 ml of tributyltin hydride are added to a solution of 1.1 g of (5R,6S)-2-(3-pyridyl)-6-[(1R)-1-allyloxycarbonyloxyethyl]-2-penem-3-carboxylic acid allyl ester in 48 ml of tetrahydrofuran. After stirring for 35 minutes at room temperature, 0.36 ml of acetic acid is added dropwise to the mixture and the whole is stirred for a further 30 minutes. The solution is concentrated in a rotary evaporator. The residue is taken up in water-/ethyl acetate and rendered neutral with NaHCO$_3$. The aqueous phase is then washed twice with ethyl acetate and concentrated under a high vacuum. Purification by chromatography on Opti UPC$_{12}$ (eluant: water) yields the title substance.

TLC (Opti UPC$_{12}$; water) R$_f$=0.61
IR (DMSO-d$_6$): 1772, 1620 cm$^{-1}$.

EXAMPLE 3

(5R,6S)-2-(6-methylpyrid-3-yl)-6-[(1R)-1-allyloxycarbonyloxyethyl]-2-penem-3-carboxylic acid allyl ester 0.3 g of 2-[(3S,4R)-3-[(1R)-1-allyloxycarbonyloxyethyl]-4-(6-methylnicotinoylthio)-2-oxo-azetidin-1-yl]-2-triphenylphosphoranylideneacetic acid allyl ester is converted into the title compound analogously to Example 1.

IR (CH$_2$Cl$_2$): 1790, 1742, 1710 cm$^{-1}$.

The starting material can be manufactured as follows:

2-[(3S,4R)-3-[(1R)-1-allyloxycarbonyloxyethyl]-4-(6-methylnicotinoylthio)-2-oxo-azetidin-1-yl]-2-triphenylphosphoranylideneacetic acid allyl ester 0.415 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester and 0.18 g of 6-methylnicotinoyl chloride hydrochloride are converted into the title compound analogously to Example 1.

IR (CH$_2$Cl$_2$): 1760, 1670, 1620, 1590 cm$^{-1}$.

EXAMPLE 4

Sodium salt of (5R,6S)-2-(6-methylpyrid-3-yl)-6-[(1R)-1-hydroxyethyl]-2-penem-3-carboxylic acid 100 mg of (5R,6S)-2-(6-methylpyrid-3-yl)-6-[(1R)-1-allyloxycarbonyloxyethyl]-2-penem-3-carboxylic acid allyl ester are converted into the title compound analogously to Example 2.

IR (DMSO-d$_6$): 1772, 1619 cm$^{-1}$.

EXAMPLE 5

(5R,6S)-2-(2-chloropyrid-3-yl)-6-[(1R)-1-allyloxycarbonyloxyethyl]-2-penem-3-carboxylic acid allyl ester 1.2 g of 2-[(3S,4R)-3-[(1R)-1-allyloxycarbonyloxyethyl]-4-(2-chloronicotinoylthio)-2-oxo-azetidin-1-yl]-2-triphenylphosphoranylideneacetic acid allyl ester are converted into the title compound analogously to Example 1.

IR (CH$_2$Cl$_2$) 1795, 1750, 1720, 1570 cm$^{-1}$.

The starting material can be manufactured as follows:

2-[(3S,4R)-3-(1R)-1-allyloxycarbonyloxyethyl]-4-(2-chloronicotinoylthio)-2-oxo-azetidin-1-yl]-2-triphenylphosphoranylideneacetic acid allyl ester 1.74 g of the silver salt of 2-[(3S,4R)-3-[(1R)-1allyloxycarbonyloxyethyl]-4-mercapto-2-oxo-azetidin-1yl]-2-triphenylphosphoranylideneacetic acid allyl ester and 0.6 g of 2-chloronicotinic acid chloride are converted into the title compound analogously to Example 1.

IR (CH$_2$Cl$_2$): 1760, 1685, 1610, 1570 cm$^{-1}$.

EXAMPLE 6

Sodium salt of (5R,6S)-2-(2-chloropyrid-3-yl)-6-[(1R)-1-hydroxyethyl]-2-penem-3-carboxylic acid 0.23 g of (5R,6S)-2-(2-chloropyrid-3-yl)-6-[(1R)-1-allyloxycarbonyloxyethyl]-2-penem-3-carboxylic acid allyl ester is converted into the title compound analogously to Example 2.

IR (DMSO-d$_6$): 1775, 1620 cm$^{-1}$.

EXAMPLE 7

(5R,6S)-2-(3-pyridyl)-6-[(1R)-1-hydroxyethyl]-2-penem-3-carboxylic acid pivaloyloxymethyl ester 62 mg of the sodium salt of (5R,6S)-2-(3-pyridyl)-6-[(1R)-1-hydroxyethyl]-2-penem-3-carboxylic acid are dissolved in 1.5 ml of absolute dimethylformamide and cooled to 0°, and 53 μl of iodomethyl pivalate are added. After stirring for 1 hour, the reaction mixture is diluted with ethyl acetate, washed three times with saturated sodium chloride solution, dried and concentrated. Column chromatography on silica gel (eluant: toluene/ethyl acetate 3:1 to 1:1) yields the title compound.

R$_f$(ethyl acetate): 0.34
IR (CH$_2$Cl$_2$): 3600, 1790, 1750, 1730, 1570 cm$^{-1}$.
UV (ethanol) $\lambda_{max}$: 340 nm.

EXAMPLE 8

(5R,6S)-2-(1-methyl-3-pyridinio)-6-[(1R)-1-hydroxyethyl]-2-penem-3-carboxylate

58 μl of dimethyl sulphate are added at pH 8 to a solution of 32 mg of the sodium salt of (5R,6S)-2-(3-pyridyl)-6-[(1R)-1-hydroxyethyl]-2-penem-3-carboxylic acid in 1.2 ml of water and 1.2 ml of dioxan. After 45 minutes, the reaction mixture is washed twice with ether. After the pH has been adjusted to 7.5, the solution is concentrated under a high vacuum and chromatographed on OPTI UPC$_{12}$ (eluant: water).

$R_f$ (water/acetonitrile 4:1): 0.54
IR (DMSO-d$_6$): 1776, 1624 cm$^{-1}$
UV (water) $\lambda_{max}$: 336 nm.

EXAMPLE 9

(5R,6S)-2-(4-pyridyl)-6-[(1R)-1-allyloxycarbonyloxyethyl]-2-penem-3-carboxylic acid allyl ester 1.5 g of 2-[(3S,4R)-3-[(1R)-1-allyloxycarbonyloxyethyl]-4-isonicotinoylthio-2-oxo-azetidin-1-yl]-2triphenylphosphoranylideneacetic acid allyl ester in 350 ml of toluene are converted into the title compound analogously to Example 1.

TLC (ethyl acetate) $R_f$=0.50
IR (CH$_2$Cl$_2$): 1795, 1745, 1715 cm$^{-1}$.

The starting material can be manufactured as follows:

2-[(3S,4R)-3-[(1R)-1-allyloxycarbonyloxyethyl]-4-isonicotinoylthio-2-oxo-azetidin-1-yl]-2-triphenylphosphoranylideneacetic acid allyl ester 3.48 g of the silver salt of 2-[(3S,4R)-3-[(1R)-1-allyloxycarbonyloxyethyl]-4-mercapto-2-oxo-azetidin-1yl]-2-triphenylphosphoranylideneacetic acid allyl ester are converted with isonicotinic acid chloride into the title compound analogously to Example 1.

TLC (ethyl acetate) $R_f$=0.30
IR (CH$_2$Cl$_2$): 1760, 1765, 1620 cm$^{-1}$.

EXAMPLE 10

Sodium salt of (5R,6S)-2-(4-pyridyl)-6-[(1R)-1-hydroxyethyl]-2-penem-3-carboxylic acid 0.71 g of (5R,6S)-2-(4-pyridyl)-6-[(1R)-1allyloxycarbonyloxyethyl]-2-penem-3-carboxylic acid allyl ester is converted into the title compound analogously to Example 2.

UV (water) $\lambda_{max}$: 341 nm
IR (DMSO-d$_6$): 3434, 1776, 1624, 1592 cm$^{-1}$.

EXAMPLE 11

(5R,6S)-2-(1-methyl-4-pyridinio)-6-[(1R)-1-hydroxyethyl]-2-penem-3-carboxylate

Analogously to Example 8, the title compound is manufactured starting from 24 mg of the sodium salt of (5R,6S)-2-(4-pyridyl)-6-[(1R)-1-hydroxyethyl]-2-penem-3-carboxylic acid.

TLC (water/acetonitrile 4:1) $R_f$=0.50
IR (DMSO-d$_6$): 1785, 1637 cm$^{-1}$
UV (water) $\lambda_{max}$: 405 nm.

EXAMPLE 12

(5R,6S)-2-(1-methoxycarbonylmethyl-3-pyridinio)-6-[(1R)-1-hydroxyethyl]-2-penem-3-carboxylate 31 mg of the sodium salt of (5R,6S)-2-(3-pyridyl)-6-[(1R)-1-hydroxyethyl]-2-penem-3-carboxylic acid are dissolved in 0.3 ml of water, and a solution of 9.3 μl of bromoacetic acid methyl ester in 0.1 ml of acetone is added. After stirring for 2 hours at room temperature and for a further 6 hours at 35°, the reaction mixture is diluted with water, and the title substance is obtained by chromatography on Opti UPC$_{12}$ (eluant: H$_2$O).

TLC (Opti UPC$_{12}$; water/acetonitrile 4:1) $R_f$=0.38
UV (water) $\lambda_{max}$=333 nm
IR (DMSO-d$_6$): 3433, 1776, 1752, 1624 cm$^{-1}$

EXAMPLE 13

(5R,6S)-2-(3-pyridyl)-6-[(1R)-1-hydroxyethyl]-2-penem-3-carboxylic acid 1-ethoxycarbonyloxyethyl ester 1.2 g of sodium iodide are dissolved in 3.7 ml of acetone, and 0.275 ml of ethyl-1-chloroethyl carbonate is added. The mixture is stirred at room temperature for 3 hours. The solution is then added dropwise to 10.5 ml of methylene chloride and the inorganic salts that are precipitated are filtered off. The methylene chloride solution is concentrated to 2 ml and, at 0°, added to a solution of 0.314 g (1 mmol) of (5R,6S)-2-(3-pyridyl)-6-[(1R)-1-hydroxyethyl]-2-penem-3-carboxylic acid in 4 ml of dimethylacetamide. The reaction mixture is then stirred for 3 hours at 0° and then diluted with ethyl acetate and washed three times with water. The organic phases are dried over sodium sulphate and concentrated in a rotary evaporator. The crude product is purified on 10 g of silica gel using ethyl acetate as eluant. The title compound is obtained in the form of a white foam.

IR spectrum (methylene chloride): 3600, 1790, 1755, 1722, 1670 cm$^{-1}$.
UV (ethanol) $\lambda_{max}$: 341 nm.

EXAMPLE 14

(5R,6S)-2-(3-pyridyl)-6-[(1R)-1-allyloxycarbonyloxyethyl]-2-penem-3-carboxylic acid allyl ester At −20°, 1.76 ml of allyloxalyl chloride and 2.43 ml of Hunig base are added in succession to a solution of 4.37 g of (3S,4R)-3-[(1R)-1-allyloxycarbonyloxyethyl]-4-nicotinoylthio-azetidin-2-one in 45 ml of dry methylene chloride. After stirring for 25 minutes at −20°, the reaction mixture is poured onto 50 ml of a pH 7 buffer solution, and the organic phase is washed with saturated sodium chloride solution and then dried and concentrated. The crude oxalic acid amide ester so obtained is stirred in 24 ml of distilled triethyl phosphite for 135 minutes at room temperature, and then 25 ml of olefin-free decane are added and the whole is concentrated under a high vacuum. This concentration with the use of decane is repeated twice. The crude phosphorane is dissolved in 40 ml of absolute toluene and stirred overnight at 110° under argon. After concentration, the title compound is purified by chromatography on silica gel (eluant: toluene) to toluene/ethyl acetate 95:5).

TLC (ethyl acetate) $R_f$=0.50
IR (CH$_2$Cl$_2$): 1795, 1747, 1715, 1575 cm$^{-1}$.

The protected penem compound so obtained is converted into the sodium salt of (5R,6S)-2-(3-pyridyl)-6-[(1R)-1-hydroxyethyl]-2-penem-3-carboxylic acid as described in Example 2.

The starting material is manufactured as follows:

(3R,4R)-3-[(1R)-1-allyloxycarbonyloxyethyl]-4-nicotinoylthio-azetidin-2-one 7 g of (3S,4R)-3-[(1R)-1-allyloxycarbonyloxyethyl]-4-acetoxy-azetidin-2-one (see European Patent Application No. 126709) and 4.2 g of thionicotinic acid are dissolved in 180 ml of methylene chloride. To this solution there are then added first 180 ml of water and then 30 ml of 1N NaOH solution. The emulsion is stirred vigorously and then stirred for 1.5 hours at room temperature. The organic phase is then separated off and the aqueous phase is extracted twice with methylene chloride. The combined organic extracts are washed with a saturated aqueous NaHCO$_3$ solution and then with saturated sodium chloride solution, dried over MgSO$_4$ and concentrated by evaporation. The resulting crude product is purified by chromatography on silica gel with toluene/ethyl acetate.

IR (CH$_2$Cl$_2$): 3400, 1780, 1743, 1670 cm$^{-1}$.

EXAMPLE 15

(5R,6S)-2-(3-pyridyl)-6-[(1R)-1-hydroxyethyl]-2-penem-3-carboxylic acid acetoxymethyl ester 63.1 mg of the sodium salt of (5R,6S)-2-(3-pyridyl)-6-[(1R)-1-hydroxyethyl]-2-penem-3-carboxylic acid are dissolved in 2 ml of absolute dimethyl formamide and 0.2 ml of absolute DMSO and, while stirring at 0°, a solution of 39.8 mg of acetoxybromomethane in 0.3 ml of absolute dimethylformamide is added dropwise thereto. After stirring for 30 minutes at 0° and then for 30 minutes at room temperature, the reaction mixture is diluted with ethyl acetate and washed twice with saturated sodium chloride solution. The organic phase is dried over magnesium sulphate and concentrated by evaporation. Purification by column chromatography (eluant: ethyl acetate) yields the title compound. IR (methylene chloride): 3585, 1792, 1765, 1728, 1580 cm$^{-1}$;

UV (ethanol) $\lambda_{max}$=339 nm.

EXAMPLE 16

(5R,6S)-2-(4-pyridyl)-6-[(1R)-1-hydroxyethyl]-3-carboxylic acid 1-ethoxycarbonyloxyethyl ester 1.2 g of sodium iodide are dissolved in 3.7 ml of acetone, and 0.275 ml of ethyl-1-chloroethyl carbonate is added. The mixture is stirred at room temperature for 3 hours. The solution is then added dropwise to 15 ml of methylene chloride and the inorganic salts that are precipitated are filtered off. The methylene chloride solution is concentrated to 2 ml and, at 0°, added to a solution of 0.291 g (1 mmol) of the sodium salt of (5R,6S)-2-(4-pyridyl)-6-[(1R)-1-hydroxyethyl]-2-penem-3-carboxylic acid in 4 ml of dimethylacetamide. The reaction mixture is then stirred at 0° for 3 hours, then diluted with ethyl acetate and washed three times with water. The organic phases are dried over sodium sulphate and concentrated in a rotary evaporator. The crude product is purified on 10 g of silica gel using ethyl acetate as eluant. The title compound is obtained in the form of a white foam.

IR spectrum (methylene chloride): 1790, 1740 cm$^{-1}$.

EXAMPLE 17

In a manner analogous to that described in the preceding Examples it is possible to manufacture the following compounds:

sodium salt of (5R,6S)-6-[(1R)-1-hydroxyethyl]-2-(6-methoxycarbonylpyrid-3-yl)-2-penem-3-carboxylic acid,
UV (water) $\lambda_{max}$ 325 nm;
IR (DMSO-d$_6$): 1771 cm$^{-1}$, sodium salt of (5R,6S)-6-[(1R)-1-hydroxyethyl]-2-(2-methoxycarbonylpyrid-3-yl)-2-penem-3-carboxylic acid,
UV (water) $\lambda_{max}$ 315 nm;
IR (DMSO-d$_6$): 1773 cm$^{-1}$, sodium salt of (5R,6S)-6-[(1R)-1-hydroxyethyl]-2-(6-hydroxypyrid-3-yl)-2-penem-3-carboxylic acid,
UV (water) $\lambda_{max}$ 323 nm;
IR (DMSO-d$_6$): 1772 cm$^{-1}$, sodium salt of (5R,6S)-6-[(1R)-1-hydroxyethyl]-2-(6-hydroxymethylpyrid-3-yl)-2-penem-3-carboxylic acid,
UV (water) $\lambda_{max}$ 325 nm;
IR (DMSO-d$_6$): 1773 cm$^{-1}$, sodium salt of (5R,6S)-6-[(1R)-1-hydroxyethyl]-2-(2-methylthiopyrid-3-yl)-2-penem-3-carboxylic acid,
UV (water) $\lambda_{max}$ 310 nm;
IR (DMSO-d$_6$): 1765 cm$^{-1}$, sodium salt of (5R,6S)-2-(6-chloropyrid-3-yl)-6-[(1R)-1-hydroxyethyl]-2-penem-3-carboxylic acid,
UV (water) $\lambda_{max}$ 328 nm;
IR (DMSO-d$_6$): 1770 cm$^{-1}$, sodium salt of (5R,6S)-2-(2-aminopyrid-3-yl)-6-[(1R)-1hydroxyethyl]-2-penem-3-carboxylic acid,
UV (water) $\lambda_{max}$ 312 nm;
IR (DMSO-d$_6$): 1768 cm$^{-1}$, sodium salt of (5R,6S)-2-(6-aminopyrid-3-yl)-6-[(1R)-1hydroxyethyl]-2-penem-3-carboxylic acid,
UV (water) $\lambda_{max}$ 325 nm;
IR (DMSO-d$_6$): 1771 cm$^{-1}$, sodium salt of (5R,6S)-2-(4-carbamoylpyrid-3-yl)-6-[(1R)-1-hydroxyethyl]-2-penem-3-carboxylic acid,
UV (water) $\lambda_{max}$ 318 nm;
IR (DMSO-d$_6$): 1773 cm$^{-1}$, sodium salt of (5R,6S)-2-(2-carbamoylpyrid-3-yl)-6-[(1R)-1-hydroxyethyl]-2-penem-3-carboxylic acid,
UV (water) $\lambda_{max}$ 315 nm;
IR (DMSO-d$_6$): 1770 cm$^{-1}$, sodium salt of (5R,6S)-2-(6-aminomethylpyrid-3-yl)-6-[(1R)-1-hydroxyethyl]-2-penem-3-carboxylic acid,
UV (water) $\lambda_{max}$ 327 nm;
IR (DMSO-d$_6$): 1771 cm$^{-1}$, sodium salt of (5R,6S)-2-(2,6-dichloropyrid-4-yl)-6-[(1R)-1-hydroxyethyl]-2-penem-3-carboxylic acid,
UV (water) $\lambda_{max}$ 321 nm;
IR (DMSO-d$_6$): 1773 cm$^{-1}$, sodium salt of (5R,6S)-2-(6-carbamoyloxymethylpyrid-3-yl)-6-[(1R)-1-hydroxyethyl]-2-penem-3-carboxylic acid,
UV (water) $\lambda_{max}$ 324 nm;
IR (DMSO-d$_6$): 1772 cm$^{-1}$, sodium salt of (5R,6S)-2-[6-(2-aminoethoxy)-pyrid-3yl]-6-[(1R)-1-hydroxyethyl]-2-penem-3-carboxylic acid,
UV (water) $\lambda_{max}$ 322 nm;
IR (DMSO-d$_6$): 1774 cm$^{-1}$, disodium salt of (5R,6S)-2-(2-carboxypyrid-3-yl)-6-[(1R)-1-hydroxyethyl]-2-penem-3-carboxylic acid,
UV (water) $\lambda_{max}$ 313 nm;
IR (DMSO-d$_6$): 1771 cm$^{-1}$, disodium salt of (5R,6S)-2-(4-carboxypyrid-3-yl)-6-[(1R)-1-hydroxyethyl]-2-penem-3-carboxylic acid,
UV (water) $\lambda_{max}$ 315 nm;
IR (DMSO-d$_6$): 1772 cm$^{-1}$, (5R,6S)-2-(1-carbamoylmethyl-3-pyridinio)-6-[(1R)-1hydroxyethyl]-2-penem-3-carboxylate,
UV (water) $\lambda_{max}$ 333 nm;
IR (DMSO-d$_6$): 3435; 1776; 1700; 1623 cm$^{-1}$, sodium salt of (5R,6S)-2-(1-carboxylatomethyl-3-pyridinio)-6-[(1R)-1-hydroxyethyl]-2-penem-3-carboxylic acid, IR (KBr): 1769; 1630: 1375 cm$^{-1}$, (5R,6S)-2-(1-cyanomethyl-3-pyridinio)-6-[(1R)-1hydroxyethyl]-2-penem-3-carboxylate, UV (water) $\lambda_{max}$ 332 nm, sodium salt of (5R,6S)-2-(4-methoxycarbonylpyrid-3-yl)-6-[(1R)-1-hydroxyethyl]-2-penem-3-carboxylic acid, UV (water) $\lambda_{max}$: 278 nm;

IR (DMSO-d$_6$): 3437; 1773; 1733; 1618 cm$^{-1}$, (5R,6S)-2-(4-cyanoethoxycarbonylpyrid-3-yl)-6-[(1R)-1hydroxyethyl]-2-penem-3-carboxylic acid, UV (water) $\lambda_{max}$: 280 nm;

IR (DMSO-d$_6$): 3431; 1772; 1737; 1617 cm$^{-1}$, sodium salt of (5R,6S)-2-(2-cyanoethoxycarbonylpyrid-3-yl)-6-[(1R)-1-hydroxyethyl]-2-penem-3-carboxylic acid, UV (water) $\lambda_{max}$: 308 nm;

IR (DMSO-d$_6$): 3433; 1773; 1738; 1619 cm$^{-1}$, (5R,6S)-2-(4-aminoethoxycarbonylpyrid-3-yl)-6-[(1R)-1hydroxyethyl]-2-penem-3-carboxylic acid, UV (water) $\lambda_{max}$: 277 nm;

IR (DMSO-d$_6$): 3400; 1772; 1687; 1572 cm$^{-1}$, (5R,6S)-2-(1-cyanoethoxycarbonylmethyl-3-pyridino)-6-[(1R)-1-hydroxyethyl]-2-penem-3-carboxylate UV (water) $\lambda_{max}$: 334 nm;

IR (KBr): 2250; 1765; 1630; 1370 cm$^{-1}$.

EXAMPLE 18

Dry-filled ampoules or phials containing 0.5 g of the sodium salt of (5R,6S)-2-(3-pyridyl)-6-[(1R)-1-hydroxyethyl]-2-penem-3-carboxylic acid as active substance, are manufactured as follows:

Composition (for 1 ampoule or phial):

| Composition (for 1 ampoule or phial): | |
| --- | --- |
| active substance | 0.5 g |
| mannitol | 0.5 g |

A sterile aqueous solution of the active substance and the mannitol is subjected to freeze-drying under aseptic conditions in 5 ml ampoules or 5 ml phials, and the ampoules or phials are sealed and checked.

Instead of the active ingredient mentioned above it is also possible to use the same amount of a different active ingredient from the preceding Examples.

I claim:

1. A compound of the formula

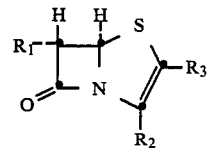

wherein
R$_1$ is hydroxymethyl or 1-hydroxyethyl;
R$_2$ is carboxy or a metabolizable esterified carboxy; and
R$_3$ is 3-pyridyl which is unsubstituted or substituted by halogen or lower alkyl,
or a pharmaceutically acceptable salt thereof.

2. (5R,6S)-2-(3-pyridyl)-6-[(1R)-1-hydroxyethyl]-2-penem-3-carboxylic acid and pharmaceutically acceptable salts thereof according to claim 1.

3. (5R,6S)-2-(6-methylpyrid-3-yl)-6-[(1R)-1-hydroxyethyl]-2-penem-3-carboxylic acid and pharmaceutically acceptable salts thereof according to claim 1.

4. (5R,6S)-2-(2-chloropyrid-3-yl)-6-[(1R)-1-hydroxyethyl]-2-penem-3-carboxylic acid and pharmaceutically acceptable salts thereof according to claim 1.

5. Esters of (5R,6S)-2-(3-pyridyl)-6-[(1R)-1-hydroxyethyl]-2-penem-3-carboxylic acid that can be cleaved under physiological conditions according to claim 1.

6. (5R,6S)-2-(3-pyridyl)-6-[(1R)-1-hydroxyethyl]-2-penem-3-carboxylic acid 1-ethoxycarbonyloxyethyl ester according to claim 1.

7. (5R,6S)-2-(3-pyridyl)-6-[(1R)-1-hydroxyethyl]-2-penem-3-carboxylic acid acetoxymethyl ester according to claim 1.

8. (5R,6S)-2-(3-pyridyl)-6-[(1R)-1-hydroxyethyl]-2-penem-3-carboxylic acid pivaloyloxymethyl ester according to claim 1.

9. The compound of claim 1 wherein
R$_1$ is (1R)-1-hydroxyethyl;
or a pharmaceutically acceptable salt thereof.

10. A pharmaceutical composition comprising an antibacterially effective amount of a compound or pharmaceutically acceptable salt thereof according to claim 1; and a pharmaceutically acceptable carrier.

11. A method of treating a bacterial infection in a mammal in need thereof comprising administering to said mammal a therapeutically effective amount of a compound of claim 1 or a pharmaceutically acceptable salt thereof.

* * * * *